US011421278B2

(12) United States Patent
Carman et al.

(10) Patent No.: US 11,421,278 B2
(45) Date of Patent: Aug. 23, 2022

(54) METHOD TO MONITOR PHARMACODYNAMIC RESPONSES MEDIATED BY IN VIVO ADMINISTRATION OF GLUCOCORTICOIDS

(71) Applicant: BRISTOL-MYERS SQUIBB COMPANY, Princeton, NJ (US)

(72) Inventors: Julie Carman, Lawrenceville, NJ (US); Yanhua Hu, Princeton, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 249 days.

(21) Appl. No.: 16/642,060

(22) PCT Filed: Aug. 28, 2018

(86) PCT No.: PCT/US2018/048240
§ 371 (c)(1),
(2) Date: Feb. 26, 2020

(87) PCT Pub. No.: WO2019/046233
PCT Pub. Date: Mar. 7, 2019

(65) Prior Publication Data
US 2020/0299770 A1 Sep. 24, 2020

Related U.S. Application Data

(60) Provisional application No. 62/551,839, filed on Aug. 30, 2017.

(51) Int. Cl.
*C12Q 1/6883* (2018.01)
(52) U.S. Cl.
CPC ..... *C12Q 1/6883* (2013.01); *C12Q 2600/106* (2013.01); *C12Q 2600/158* (2013.01)
(58) Field of Classification Search
None
See application file for complete search history.

(56) References Cited

U.S. PATENT DOCUMENTS

2007/0054309 A1\* 3/2007 Hakonarson ......... C12Q 1/6809
435/6.18

OTHER PUBLICATIONS

Menke et al Neuropsychopharmacology. 2012. 37: 145-1464 (Year: 2012).\*
Galon J et al., Gene profiling reveals unknown enhancing and suppressive actions of glucocorticoids on immune cells, The Faseb Journal, Federation of American Societies for Experimental Biology, US, 16:16 1-71 (Jan. 1, 2002), XP002240642, ISSN: 0892-6638, DOI: 10.1096/FJ.01-0245COM.
Hakonarson Hakon et al., Profiling of genes expressed in peripheral blood mononuclear cells predicts glucocorticoid sensitivity in asthma patients, Proceedings of the National Academy ofsciences of the United States of America, 102:41 14789-14794 (Oct. 11, 2005), XP002786367, ISSN: 0027-8424 abstract.
Hu Yanhua et al., Development of a Molecular Signature to Monitor Pharmacodynamic Responses Mediated by In Vivo Administration of Glucocorticoids, Arthritis & Rheumatology, 70:8,13 1331-1342 (Mar. 13, 2018), XP002786368.
Hu Yanhua Sarah et al., Gene Signature for Glucocorticoid, from in Vitro to In Vivo (Abstract No. 759), Arthritis & Rheumatology, 68:10 (2016), XP002786366 and Annual Meeting of the American-College-of-Rheumatology/ Association-of-Rheumatology-Health-Professionals (ACR/ARHP); Washington, DC, USA; Nov. 11-16, 2016.
Toonen E J M et al., Gene expression profiling in rheumatoid arthritis: Current concepts and future directions, Annals of the Rheumatic Oise, British Medical Association, GB, 67:12 1663-1669 (Dec. 1, 2008), XP009183610, ISSN: 0003-4967, DOI: 10.1136/ARD.2007.076588 abstract.
Toonen Erik J M et al., Prednisolone-induced changes in gene-expression profiles in healthy volunteers, Pharmacogenomics 12:7 985-998 (2011), XP009509199, ISSN: 1744-8042.
Menke, Andreas, et al., "Dexamethasone Stimulated Gene Expression in Peripheral Blood is a Sensitive Marker for Glucocorticoid Receptor Resistance in Depressed Patients", Neuropsychophamacology, 2012, 37, 1455-1464.

\* cited by examiner

*Primary Examiner* — Carla J Myers

(57) ABSTRACT

The present invention relates generally to a method of monitoring pharmacodynamic responses mediated by in vivo administration of glucocorticoids. More specifically, the present invention relates to a method of using a change in gene signature as a pharmacodynamic marker of glucocorticoid exposure.

12 Claims, 13 Drawing Sheets

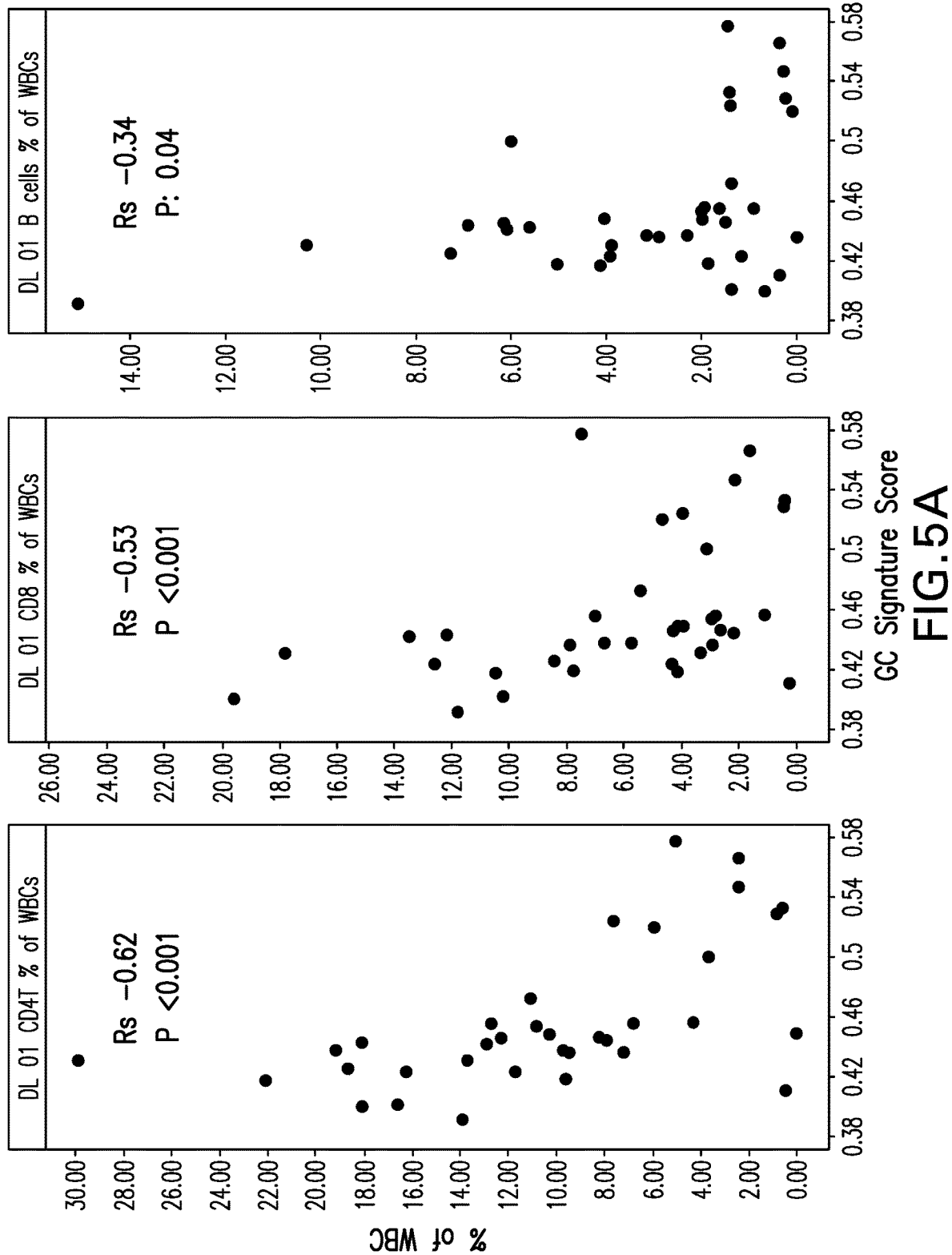

METHOD TO MONITOR PHARMACODYNAMIC RESPONSES MEDIATED BY IN VIVO ADMINISTRATION OF GLUCOCORTICOIDS

CROSS REFERENCE TO RELATED APPLICATIONS

This application is a national phase application under 35 U.S.C. § 371 of International Patent Application No. PCT/US18/48240, filed Aug. 28, 2018, which claims the benefit under 35 U.S.C. § 119(e) of U.S. Provisional Application Ser. No. 62/551,839, filed Aug. 30, 2017; the disclosure of which is incorporated herein by reference.

Throughout this application various publications are referenced. The disclosures of these publications in their entireties are hereby incorporated by reference into this application in order to more fully describe the state of the art to which this invention pertains.

FIELD OF THE INVENTION

The present invention relates generally to a method of monitoring pharmacodynamic responses mediated by in vivo administration of glucocorticoids.

BACKGROUND OF THE INVENTION

Glucocorticoids (GCs) are effective anti-inflammatory drugs that are used extensively to treat many human diseases, including rheumatoid arthritis (RA), inflammatory bowel diseases, psoriasis, asthma, and systemic lupus erythematosus (SLE) (Buttgereit F. Bull NYU Hosp Jt Dis 2012; 70 Suppl 1:S26-9). However, their utility is limited by the toxicities of these drugs which include diabetes, osteoporosis, muscle wasting, fat redistribution, and suppression of the hypothalamic-pituitary-adrenal gland (HPA) axis (Desmet S J, et. al., J Clin Invest 2017; 127:1136-45). The risk for harmful side effects increases with higher doses and more prolonged use (Bijlsma J W J, et. al. Rheumatology 2016; 55 Suppl 2:ii3-5; Ruiz-Arruza I, et. al. Rheumatology 2014; 53:1470-6). Despite the potential for adverse effects, Glucocorticoids remain a key standard-of-care treatment. Glucocorticoids mediate their biologic effects via interactions with a nuclear hormone receptor, glucocorticoid receptor alpha (GR). Glucocorticoid receptor alpha is a ligand-activated transcription factor that induces transcription by binding as a homodimer to glucocorticoid-responsive elements (Weikum E R, et. al. Nat Rev Mol Cell Biol 2017; 18:159-74). Many GR-activated genes have anti-inflammatory activity (Colotta F, et. al. Science 1993; 261:472-5; Abraham S M, et. al. J Exp Med 2006; 203:1883-9; Beaulieu E, et. al. Nat Rev Rheum 2011; 7:340-8). However, trans-activated genes are also associated with side effects (Cain D W, et. al. Nat Rev Immunol 2017; 17:233-47). GR has also been shown to inhibit the activity of several pro-inflammatory transcription factors including NF-κB, AP-1, IR3F, CREB, NFAT, STAT, T-Bet, and Gata-3, independently of DNA binding in a process referred to as transrepression (Greulich F, et. al. Steroids 2016; 114:7-15). Several synthetic glucocorticoids have been developed with reduced transactivation but intact transrepression activity in an attempt to broaden the therapeutic window (Strehl C, et. al., Exp Opin Invest Drugs 2017; 26:187-95).

In addition to the risk of developing damaging effects, chronic glucocorticoid use is also associated with tissue-specific resistance (Rodriguez J M, et. al., Steroids 2016; 115:182-92). Several resistance mechanisms have been described, including downregulation of GR expression as well as upregulation of a dominant negative isoform of the receptor (Dendoncker K, et. al. Cytokine Growth Factor Rev 2017; 35:85-96). Polymorphisms of the GR that modulate sensitivity to agonists have also been described (Straub R H, et. al. Rheumatology 2016; 55 Suppl 2:ii6-14). Given the heterogeneity of clinical responses to glucocorticoids, it would be extremely valuable to have a companion biomarker of glucocorticoid biologic activity.

SUMMARY OF INVENTION

The inventors developed a gene signature based on genes modulated by treatment of peripheral blood mononuclear cells (PBMCs) from normal healthy volunteer (NHV) donors with prednisolone. Sensitivity of this signature was confirmed by analyzing whole-blood gene expression in healthy participants post-dosing with either prednisolone or a partial GR agonist. Expression of the signature was higher in healthy subjects dosed with prednisolone than in those who received the partial agonist, in alignment with the transactivation potential of the compound. Expression of the signature in whole blood from patients with systemic lupus erythematosus (SLE) and rheumatoid arthritis (RA) correlated with known glucocorticoid-mediated pharmacodynamic effects, including higher levels of peripheral blood neutrophils and lower levels of peripheral blood lymphocytes. Expression of the signature also aligned with reported use and dose of prednisolone in these cohorts.

The invention comprises a method to determine a person's response to glucocorticoids comprising administering the glucocorticoid of interest to said person, drawing blood from the person administered the glucocorticoid of interest, isolating the RNA from the collected blood, profiling the gene expression of the isolated RNA, and comparing the gene signature score post-administration with a control gene signature score, wherein an increase in the gene signature score for FKBP5, ECHDC3, IL1R2, ZBTB16, IRS2, IRAK3, ACSL1, DUSP1 indicates a response to the glucocorticoid.

The invention comprises a method to determine a person's response to glucocorticoids comprising administering the glucocorticoid of interest to said person, drawing blood from the person administered the glucocorticoid of interest, isolating the RNA from the collected blood, profiling the gene expression of the isolated RNA, and comparing the gene signature score post-administration with a control gene signature score, wherein an increase in the gene signature score for FKBP5, ECHDC3, IL1R2, ZBTB16, IRS2, IRAK3, ACSL1, DUSP1, PHC2, TLR2, TSC22D3, SLA, CRISPLD2, MAN2A2, FAR2, CEBPD, SPTLC2, HSPA6 indicates a response to the glucocorticoid.

The invention comprises a method to determine a person's response to glucocorticoids comprising administering the glucocorticoid of interest to said person, drawing blood from the person administered the glucocorticoid of interest, isolating the RNA from the collected blood, profiling the gene expression of the isolated RNA, and comparing the gene signature score post-administration with a control gene signature score, wherein an increase in the gene signature score for FKBP5, ECHDC3, IL1R2 indicates a response to the glucocorticoid.

The invention comprises a method to determine a person's response to glucocorticoids comprising administering the glucocorticoid of interest to said person, drawing blood from the person administered the glucocorticoid of interest, isolating the RNA from the collected blood, profiling the gene expression of the isolated RNA, and comparing the gene signature score post-administration with a control gene signature score, wherein an increase in the gene signature score for FKBP5, ECHDC3, IL1R2, ZBTB16, IRS2, IRAK3 indicates a response to the glucocorticoid.

In an embodiment of the invention, the glucocorticoid of interest is cortisone, dexamethasone, hydrocortisone, methylprednisolone, prednisolone, prednisone, triamcinolone, betamethasone budesonide, fluticasone, and/or synthetic glucocorticoids.

In an embodiment of the invention, the control gene signature score is derived from blood collected from the same person pre-glucocorticoid-administration and/or blood collected from normal healthy controls not administered the glucocorticoid.

In an embodiment of the invention, the blood sample is collected from the person administered the glucocorticoid of interest 4 hours post-administration.

In an embodiment of the invention, the person who responds to the glucocorticoid of interest has a gene signature score at least 1.5-fold greater than the control.

In an embodiment of the invention, the person who responds to the glucocorticoid of interest has a gene signature score at least 2-fold greater than the control.

The invention comprises a method of treating a person diagnosed with SLE or RA comprising 1) determining the person's response to glucocorticoids by administering the glucocorticoid of interest to the person, drawing blood from the person administered the glucocorticoid of interest, isolating the RNA from the collected blood, profiling the gene expression of the isolated RNA, and 2) comparing the gene signature score post-administration with a control gene signature score, wherein an increase in the gene signature score for FKBP5, ECHDC3, IL1R2, ZBTB16, IRS2, IRAK3, ACSL1, DUSP1 indicates the person will respond to the glucocorticoid of interest and 3) administering the glucocorticoid to the person.

The invention comprises a method of treating a person diagnosed with SLE or RA comprising 1) determining the person's response to glucocorticoids by administering the glucocorticoid of interest to said person, drawing blood from the person administered the glucocorticoid of interest, isolating the RNA from the collected blood, profiling the gene expression of the isolated RNA, and 2) comparing the gene signature score post-administration with a control gene signature score, wherein in increase in the gene signature score for FKBP5, ECHDC3, IL1R2, ZBTB16, IRS2, IRAK3, ACSL1, DUSP1, PHC2, TLR2, TSC22D3, SLA, CRISPLD2, MAN2A2, FAR2, CEBPD, SPTLC2, HSPA6 indicates the person will respond to the glucocorticoid of interest and 3) administering the glucocorticoid to the person.

The invention comprises a method of treating a person diagnosed with SLE or RA comprising 1) determining the person's response to glucocorticoids by administering the glucocorticoid of interest to said person, drawing blood from the person administered the glucocorticoid of interest, isolating the RNA from the collected blood, profiling the gene expression of the isolated RNA, and 2) comparing the gene signature score post-administration with a control gene signature score, wherein an increase in the gene signature score for FKBP5, ECHDC3, IL1R2, indicates the person will respond to the glucocorticoid of interest and 3) administering the glucocorticoid to the person.

The invention comprises a method of treating a person diagnosed with SLE or RA comprising 1) determining the person's response to glucocorticoids by administering the glucocorticoid of interest to said person, drawing blood from the person administered the glucocorticoid of interest, isolating the RNA from the collected blood, profiling the gene expression of the isolated RNA, and 2) comparing the gene signature score post-administration with a control gene signature score, wherein an increase in the gene signature score for FKBP5, ECHDC3, IL1R2, ZBTB16, IRS2, IRAK3, indicates the person will respond to the glucocorticoid of interest and 3) administering the glucocorticoid to the person.

P=0.003, *P<0.001. (4B) GC gene signature scores for baseline samples from an abatacept SLE phase II trial. Patients were categorized by GC dose (low, medium, or high). ns=not significant; **P=0.001.

Figure 5B:
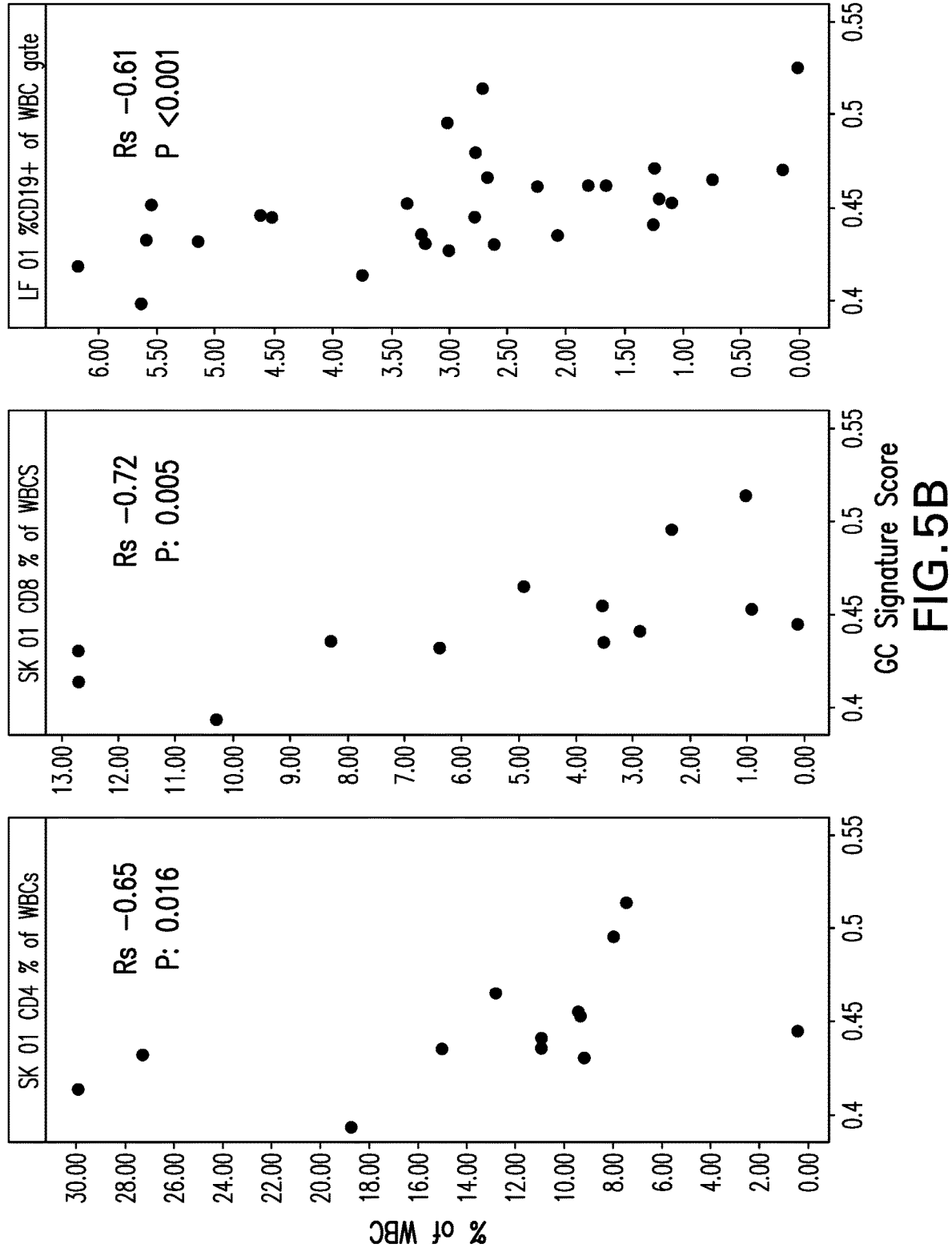
Figure 5C:
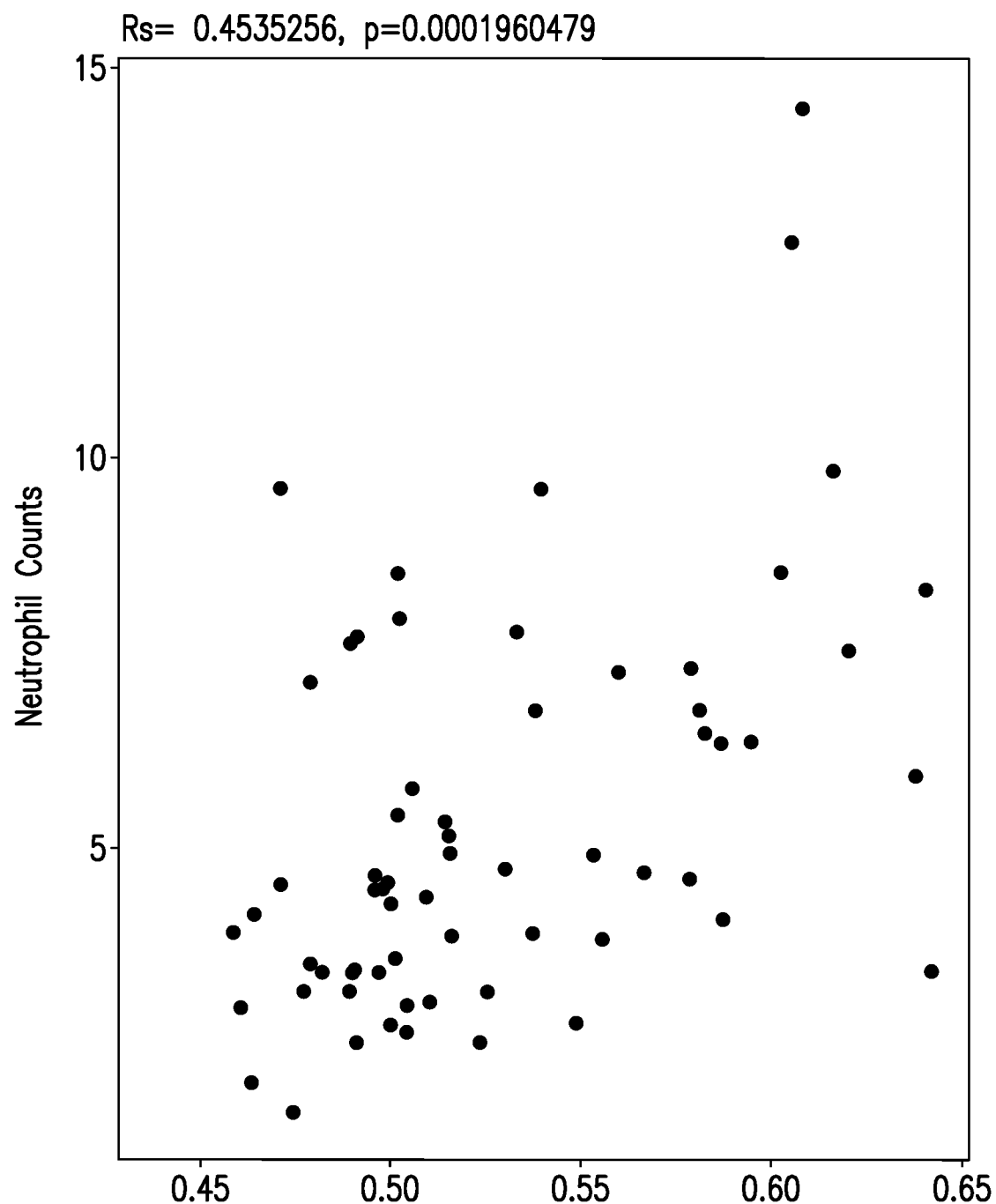

FIG. 5A-5C shows GC gene signature correlates. The percentages of peripheral blood CD4+ T cells, CD8+ T cells, and CD19+ B cells from patients with SLE (5A) and RA (5B) are plotted relative to the GC gene signature score for each patient. WBC=white blood cell. (5C) Peripheral blood neutrophil counts from the abatacept SLE trial baseline samples are plotted relative to the GC gene signature score for each patient. Correlations were analyzed by the Spearman ranked test.

Figure 6A:
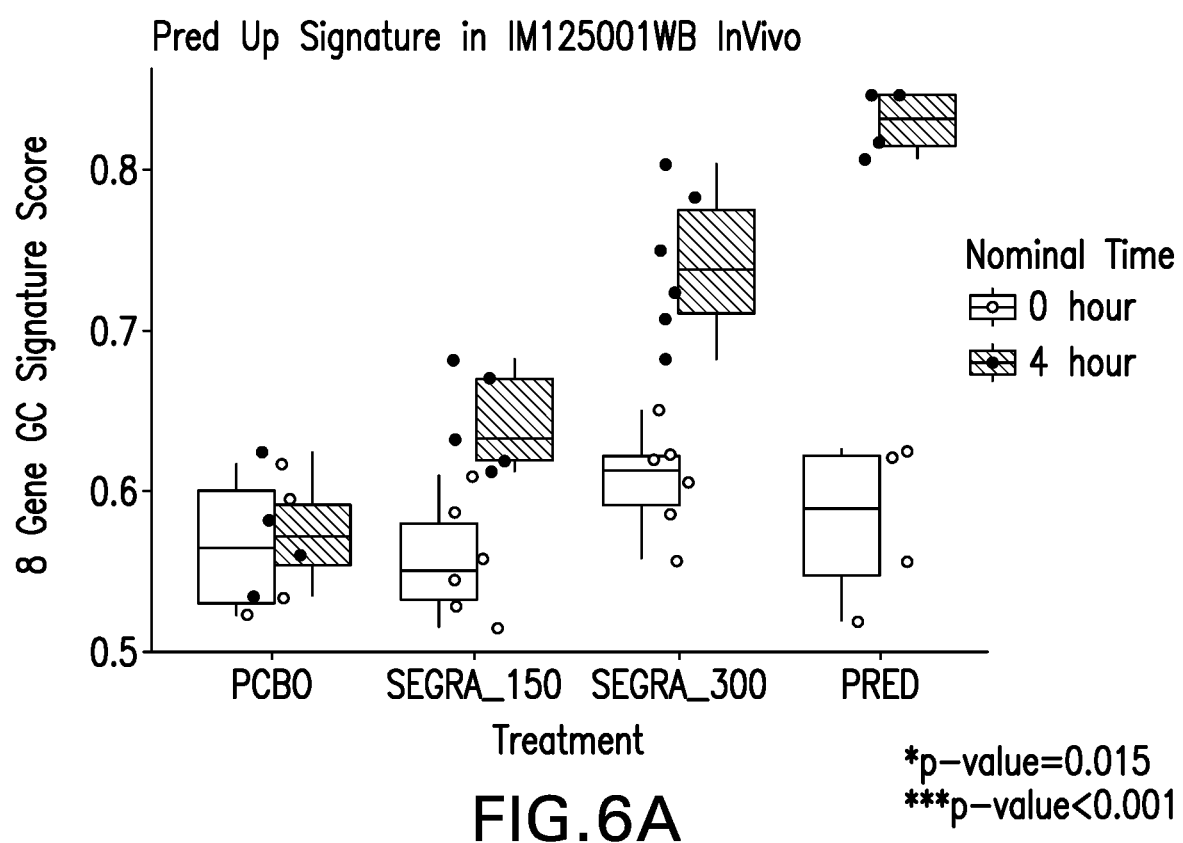
Figure 6B:
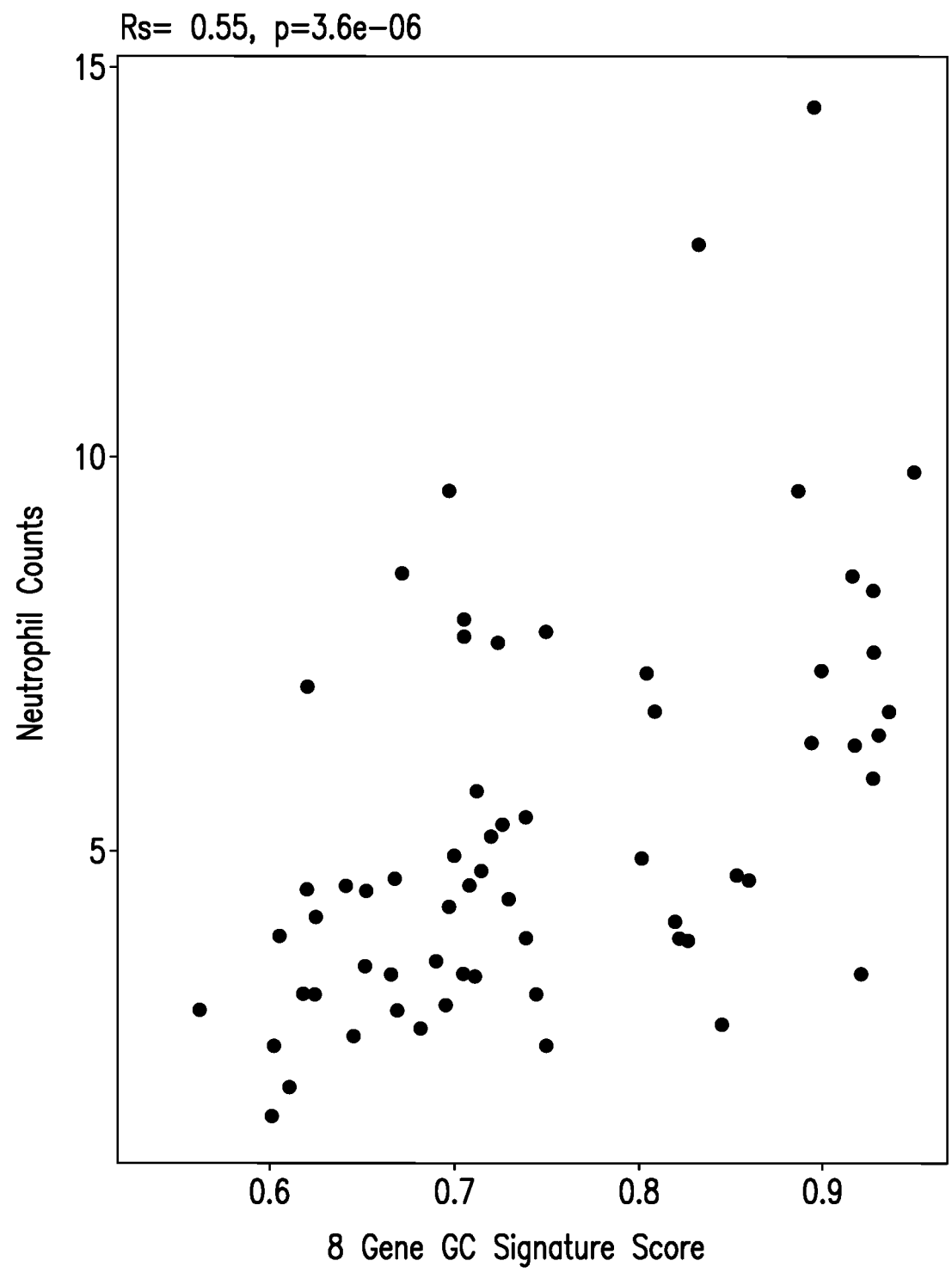

FIG. 6A-6B shows validation of the 8-gene GC signature. (6A) GC gene signature scores using an abbreviated list of 8 genes for participants from the Prednisoline in Healthy Male cohort 2 administered placebo, 150 or 300 mg GR modulator BMS-791826, or 10 mg prednisolone. *P=0.015; ***P<0.001. (6B) GC gene signature scores using the 8-gene list versus peripheral blood neutrophil counts for participants at baseline from the abatacept SLE study. The correlation was calculated using the Spearman ranked test.

DETAILED DESCRIPTION OF THE INVENTION

Glucocorticoids are administered as described in the Prescribing Information for each drug. In general, the initial dose is determined by the severity of the specific disease entity being treated. In situations of less severity, lower doses will generally suffice while in selected patients higher initial doses may be required. The initial dosage is typically maintained or adjusted until a satisfactory response is noted. If after a reasonable period of time, there is a lack of satisfactory clinical response, the glucocorticoid is discontinued and the patient placed on other appropriate therapy. After a favorable response is achieved, the proper maintenance dosage is determined by decreasing the initial drug dosage in small decrements at appropriate time intervals until the lowest dosage that will maintain an adequate clinical response is reached. Clearly, being able to determine how a patient is going to respond to a glucocorticoid would decrease the time required to optimize a patient's maintenance dose.

The invention comprises a method to determine a person's response to glucocorticoids by administering the glucocorticoid of interest to the person, drawing blood from the person administered the glucocorticoid of interest, isolating the RNA from the collected blood, profiling the gene expression of the isolated RNA, and comparing the gene signature post-administration with a control gene signature, wherein upregulation of selected genes indicates a response to the glucocorticoid.

The inventors discovered that the expression of the glucocorticoid gene signature is significantly elevated in peripheral blood leukocytes of normal healthy volunteers (NHVs) following oral administration of the glucocorticoid. Expression of the signature increased dose-dependently, peaked at 4 hours post administration, and returned to baseline by 48 hours post-dose. Lower expression is detected in NHVs who are administered a partial glucocorticoid receptor agonist, consistent with the reduced transactivation potential of this compound. In cohorts of patients with systemic lupus erythematosus (SLE) and rheumatoid arthritis (RA), expression of the glucocorticoid signature is negatively correlated with percentages of peripheral blood lymphocytes and positively correlated with peripheral blood neutrophil counts, consistent with the known biology of the glucocorticoid receptor.

Identification of Glucocorticoid-Regulated Genes

In order to monitor glucocorticoid-dependent responses in peripheral blood, genes modulated by prednisolone in human PBMCs were identified. PBMCs from 10 independent normal healthy volunteer donors were treated with either DMSO control or 1 µM prednisolone for 6 hours. Genes with >2-fold change and a FDR-corrected P value of <0.05 were identified as upregulated or downregulated genes.

Figure 1A:
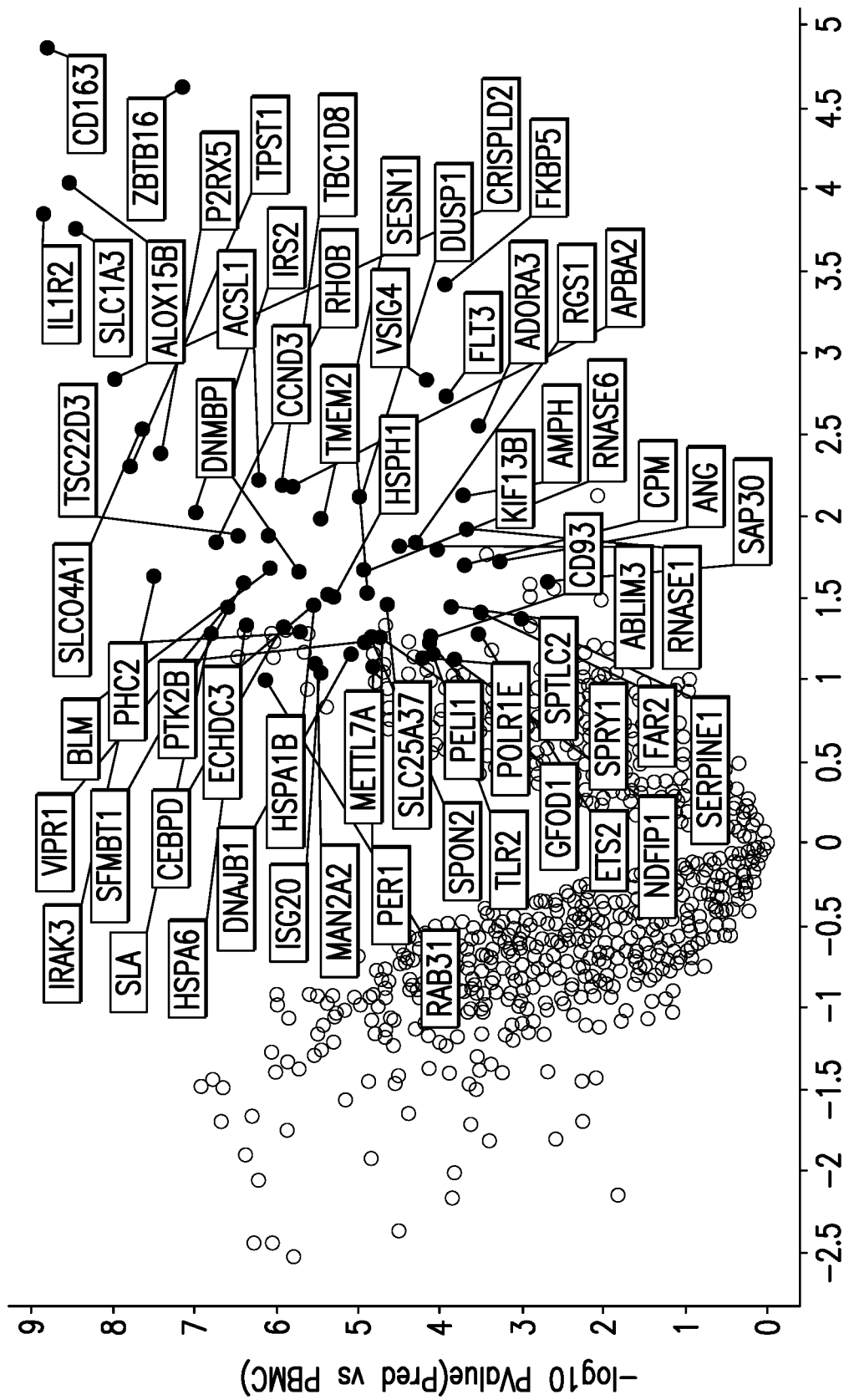
FIG. 1A-1D shows the glucocorticoid (GC)-regulated genes. Peripheral blood mononuclear cells (PBMCs) from normal healthy volunteers (NHVs) were cultured in vitro for 6 hours with either 1 µM prednisolone or DMSO vehicle alone. RNA was analyzed for gene expression using Affymetrix profiling. Analyses of genes modulated by prednisolone as compared with vehicle are shown. Axes represent the FDR-adjusted log 10 P value versus fold change. Genes upregulated (1A) and downregulated (1B)>2-fold by prednisolone versus vehicle with an FDR-adjusted P value of ≤0.05 are shown. ssGSEA scores for upregulated (1C) and downregulated (1D) genes for whole blood samples stimulated with increasing concentrations of prednisolone in vitro. P=0.005, *P<0.001.

The upregulated genes include ECHDC3, ACSL1, P2RX5, TPST1, TBC1D8, APBA2, SESN1, RNASE1, ABLIM3, RNASE6, BLM, KIF13B, DNMBP, SAP30, SFMBT1, TMEM2, HSPH1, METTL7A, HSPA1B, SLC25A37, VIPR1, FAR2, HSPA6, PHC2, PELI1, POLR1E, SPON2, GFOD1, SPRY1, NDFIP1, MAN2A2, ISG20, RAB31; FKBP5, IL1R2, ZBTB16, IRS2, IRAK3, DUSP1, SLCO4A1, TSC33D3, CD163, SLC1A3, ALOX15B, CCND3, RHOB, VSIG4, FLT3, CRISPLD2, ADORA3, RGS1, AMPH, CPM, ANG, CD93, SPTLC2, SERPINE1, ESTS2, TLR2, PER1, DNAJB1, PTK2B, CEBPD, SLA (FIG. 1A).

Figure 1B:
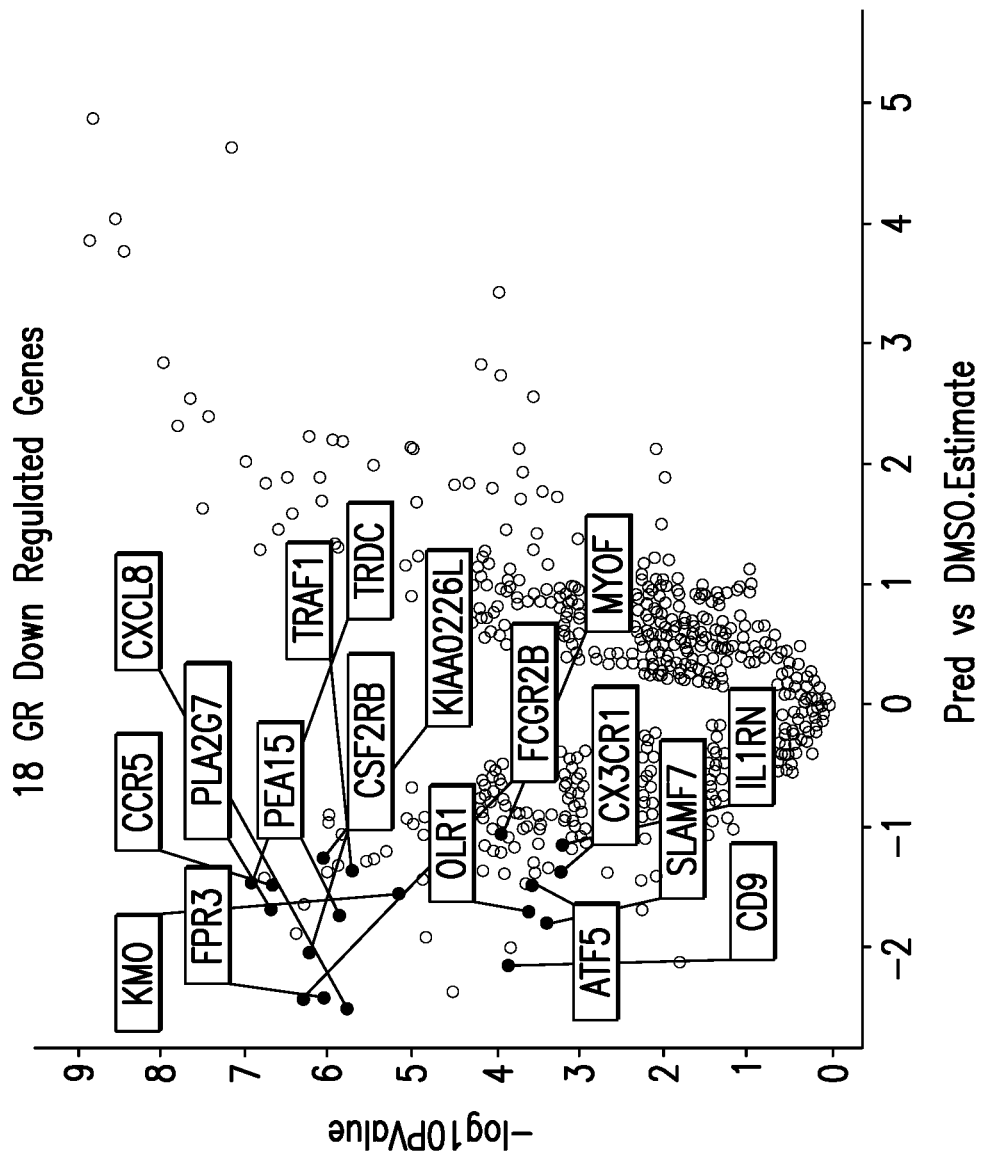

The downregulated genes include KMO, CCR5, CXCL8, FPR3, PLA2G7, PEA15, TRAF1, CSF2RB, TRDC, OLR1, KIAA0226L, FCGR2B, ATFS, CX3CR1, MYOF, SLAMF7, CD9, IL1RN (FIG. 1B).

Figure 1C:
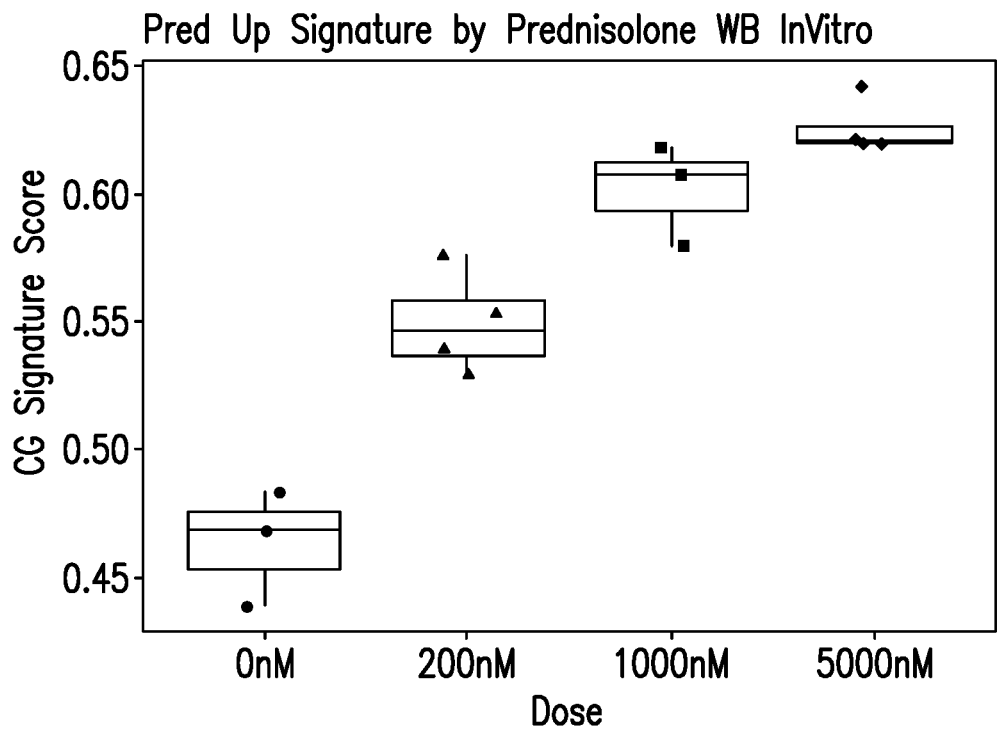
Figure 1D:
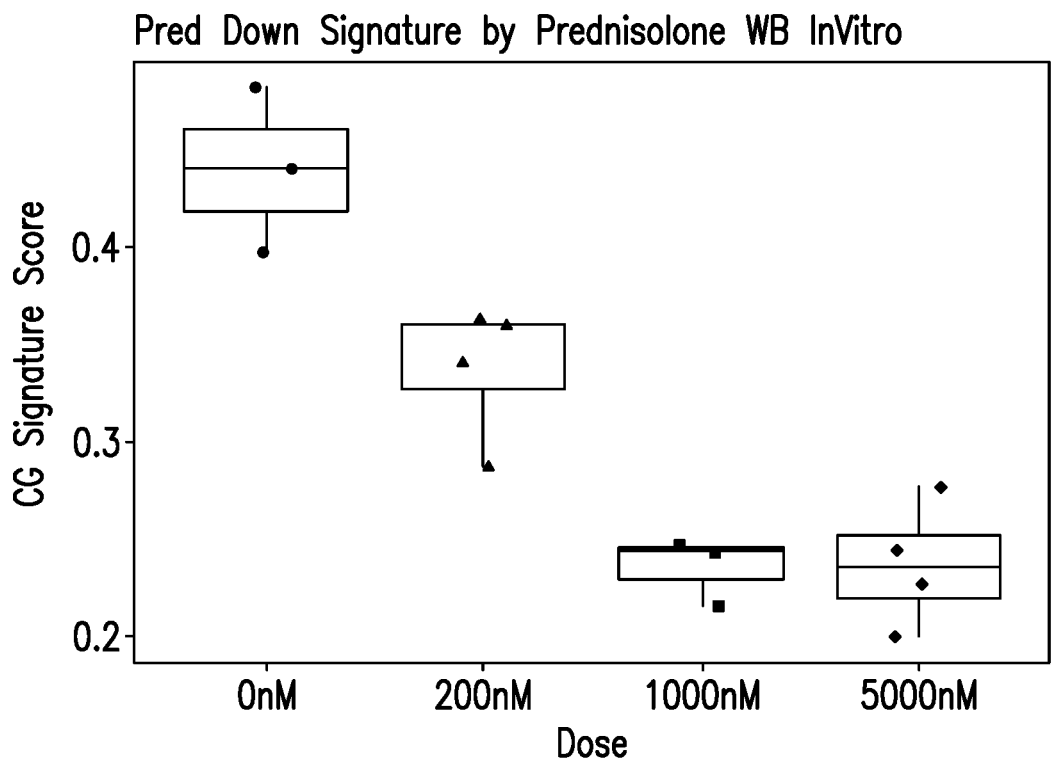

Many of these genes were known glucocorticoid-regulated genes (Chinenov Y, et. al., BMC Genomics 2014; 15:656). However, upregulated genes ECHDC3, ACSL1, P2RX5, TPST1, TBC1D8, APBA2, SESN1, RNASE1, ABLIM3, RNASE6, BLM, KIF13B, DNMBP, SAP30, SFMBT1, TMEM2, HSPH1, METTL7A, HSPA1B, SLC25A37, VIPR1, FAR2, HSPA6, PHC2, PELI1, POLR1E, SPON2, GFOD1, SPRY1, NDFIP1, MAN2A2, ISG20, RAB31 have not been previously linked to glucocorticoid regulation. Several of the upregulated genes have previously been associated with anti-inflammatory activity, including DUSP1 (Abraham S M, et. al., J Exp Med 2006; 203:1883-9), TSC22D3 (Beaulieu E, et. al. Nat Rev Rheum 2011; 7:340-8), IRAK3 (Miyata M, et. al., Nat Commun 2015; 6:606), and CD163 (Schaer D J, et. al., Immunogenetics 2001; 53:170-7), while several of the downregulated genes encoded chemokines, chemokine receptors, and other pro-inflammatory mediators. Network analysis of the regulated genes indicated enrichment for immune-response pathways. Single-sample gene set enrichment analysis (ssGSEA) algorithm was used to generate a composite score (or gene signature) for enrichment of these genes in the transcriptomes of individual samples (Barbie D A, et. al. Nature 2009; 462:108-12). Whole blood was stimulated with different concentrations of prednisolone in vitro for 5 hours, and the expression levels of up- and downregulated genes were calculated. The ssGSEA score for the upregulated genes increased dose dependently (FIG. 1C). Similarly, the expression of the downregulated genes decreased in a dose-dependent manner (FIG. 1D). The upregulated gene module had a larger dynamic range, and therefore this gene module was utilized for all other analyses.

Figure 2A:
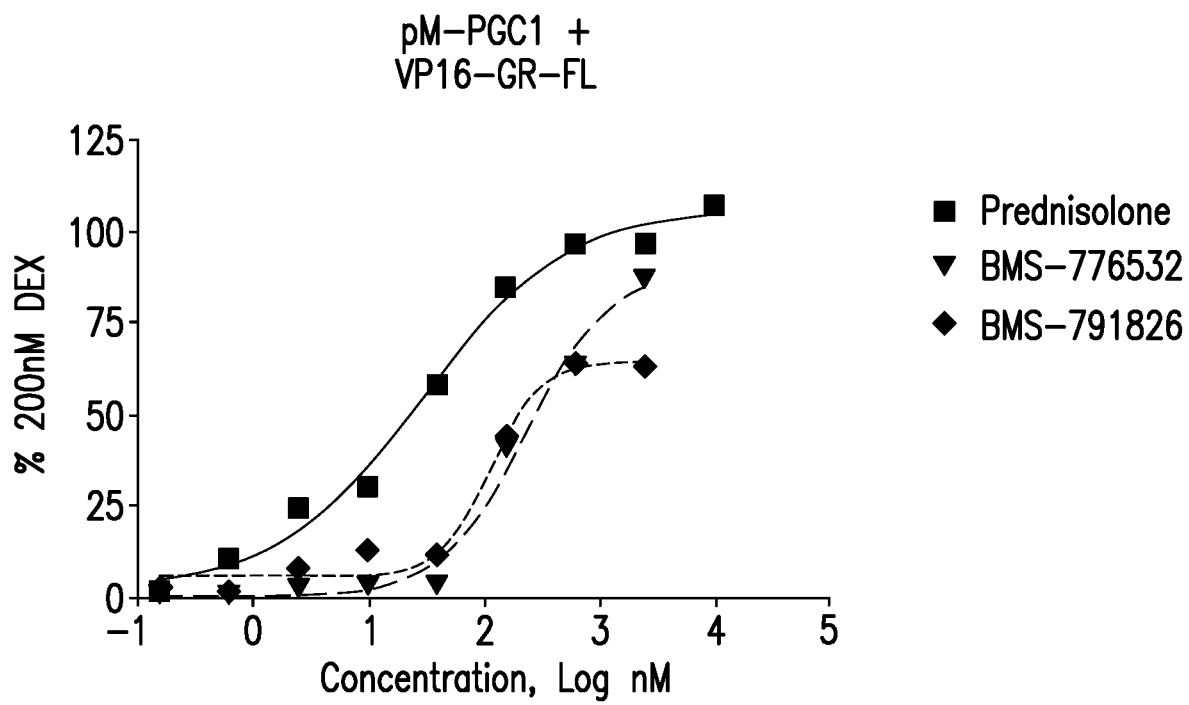
FIG. 2A-2E shows the validation of the glucocorticoid gene signature using partial GR agonists. Mammalian 2-hybrid analysis of PGC1 (2A) and TIF2 (2B) recruitment by prednisolone, GR modulators BMS-791826, and BMS-776532. Data represent the mean value of triplicates normalized to the activity induced by 200 nM dexamethasone. One representative experiment of 2 is shown. Analysis of GR (2C) and TIF2 (2D) recruitment to the promoters of ANGPTL4, ALOX5AP, and LEPREL1 by 1 µM prednisolone, 1 µM GR modulators BMS-791826, and 2 µM BMS-776532 as analyzed by chromatin immunoprecipitation followed by qPCR. Values represent the mean and standard deviations of triplicate reactions. Binding values are normalized to input values. ChIP=chromatin immunoprecipitation. P values were calculated by T test. *P<0.01 vs prednisolone, P<0.01 vs prednisolone, *P<0.001 vs prednisolone, ns=not significant. (2E) GC gene signature scores for whole blood samples cultured in vitro with either DMSO vehicle, 5 µM prednisolone, 5 µM GR modulators BMS-791826, or 10 µM BMS-776532. ***P<0.001
Figure 2B:
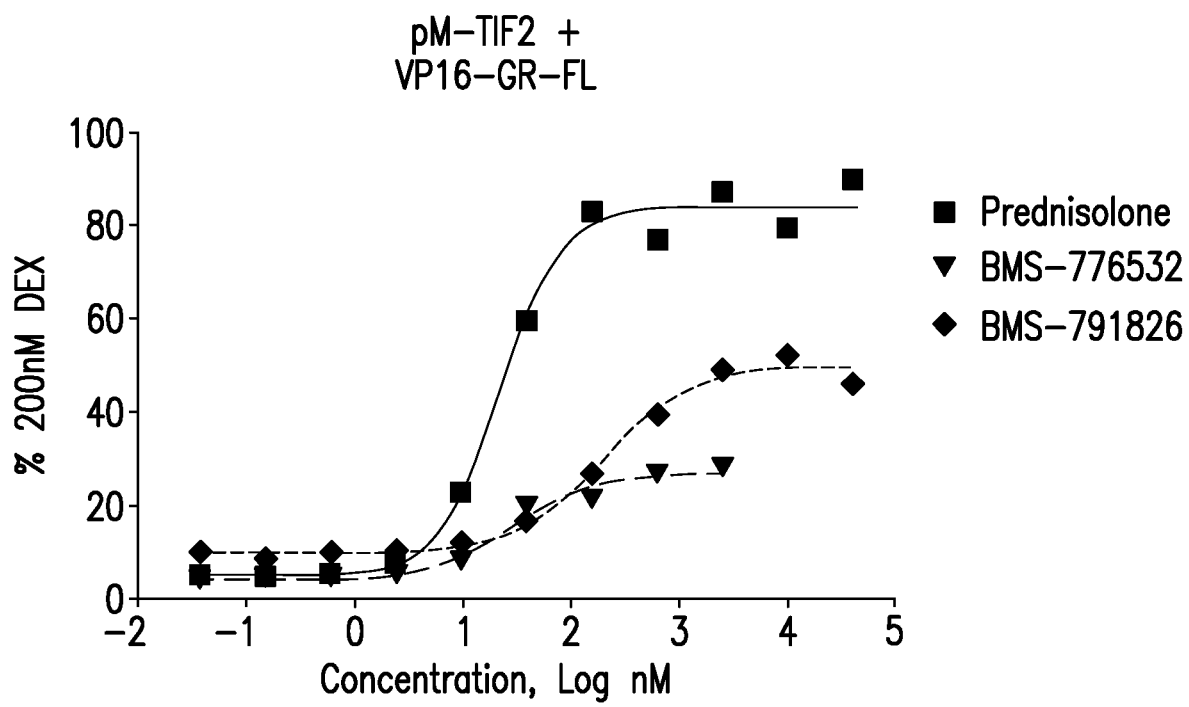
Figure 2C:
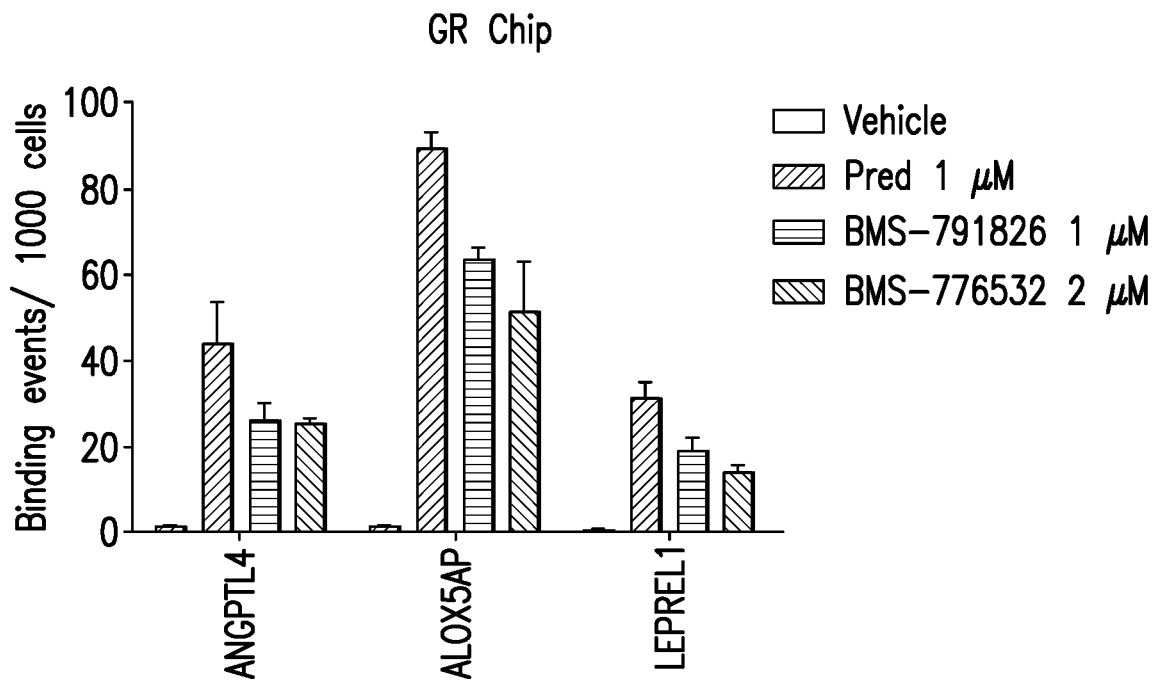
Figure 2D:
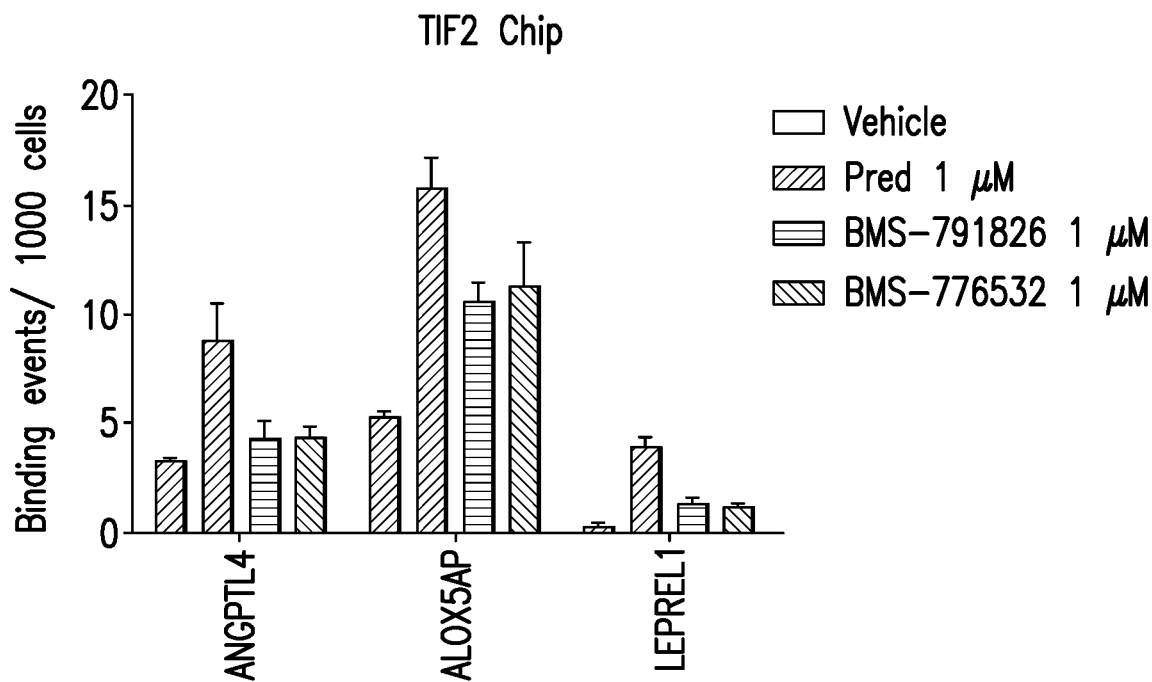
Figure 2E:
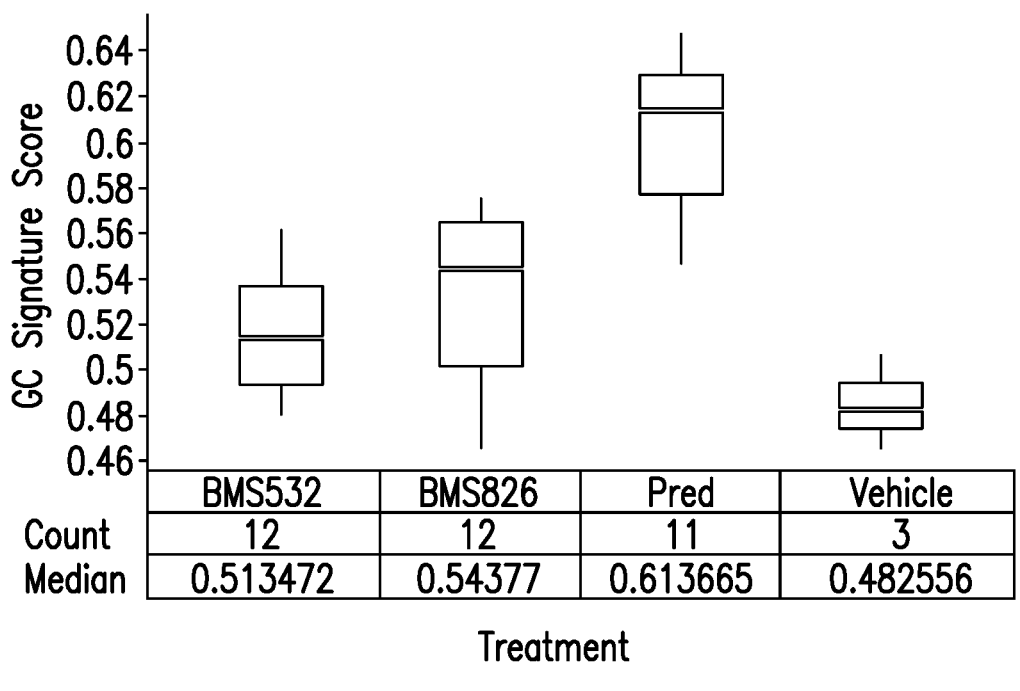

In order to provide further mechanistic evidence that this gene module accurately reflects GR activity, the activity of partial glucocorticoid receptor (GR) agonists was analyzed. In vitro and in vivo activities of two selective GR modulators, BMS-776532 and BMS-791826 have been previously described (Weinstein D S, et. al. J Med Chem 2011; 54:7318-33). Both compounds bound to GR and repressed AP-1- and nuclear factor-κB-dependent reporters, but demonstrated significantly weaker induction of a GR-dependent reporter as compared with prednisolone. BMS-791826 was more potent in transrepression and transactivation assays as compared with BMS-776532. The GR modulates transcription via recruitment of co-regulators including TIF2 (Khan S H, et. al., Biol. Chem. 2012; 287:44546-44560) and PGC1α (Knutti D, et. al., Mol. Cell. Biol. 2000; 20:2411-2422). A mammalian 2-hybrid system as well as chromatin immunoprecipitations were used to characterize the transactivation potential of these compounds. Compared to prednisolone, BMS-791826 and BMS-776532 recruited significantly less PGC1α and TIF2 to the GR, peaking at 30-75% of the level recruited by prednisolone (FIG. 2A, 2B). BMS-791826 recruited more TIF2 (50% vs 30%) but similar amounts of PGC1α as compared with BMS-776532. In a chromatin immunoprecipitation assay, both compounds recruited significantly lower amounts of GR (FIG. 2C) as well as TIF2 (FIG. 2D) to the promoters of three target genes as compared with prednisolone confirming the reduced transactivation potential of these compounds. Whole blood from two independent normal healthy volunteer donors was stimulated in vitro with these compounds and prednisolone for 5 hours followed by RNA isolation and Affymetrix profiling. The glucocorticoid gene signature scores for these samples aligned well with the transactivation potential of the compounds: prednisolone>BMS-791826>BMS-776532 (FIG. 2E).

The invention comprises a method to determine a person's response to glucocorticoids comprising stimulating whole blood collected from a person in need thereof with the glucocorticoid of interest, isolating the RNA from the stimulated blood, profiling the gene expression of the isolated RNA, and comparing the gene signature score post-stimulation with a control gene signature score, wherein the gene signature comprises genes ECHDC3, ACSL1, P2RX5, TPST1, TBC1D8, APBA2, SESN1, RNASE1, ABLIM3, RNASE6, BLM, KIF13B, DNMBP, SAP30, SFMBT1, TMEM2, HSPH1, METTL7A, HSPA1B, SLC25A37, VIPR1, FAR2, HSPA6, PHC2, PELI1, POLR1E, SPON2, GFOD1, SPRY1, NDFIP1, MAN2A2, ISG20, RAB31, wherein an increase in the gene signature score indicates a response to the glucocorticoid.

The invention comprises a method to determine a person's response to glucocorticoids comprising stimulating whole blood collected from a person in need thereof with one or more glucocorticoids selected from the group consisting of cortisone, dexamethasone, hydrocortisone, methylprednisolone, prednisolone, prednisone, triamcinolone, betamethasone budesonide, fluticasone, and synthetic glucocorticoids, isolating the RNA from the stimulated blood, profiling the gene expression of the isolated RNA, and comparing the gene signature score post-stimulation with a control gene signature score, wherein the gene signature comprises genes ECHDC3, ACSL1, P2RX5, TPST1, TBC1D8, APBA2, SESN1, RNASE1, ABLIM3, RNASE6, BLM, KIF13B, DNMBP, SAP30, SFMBT1, TMEM2, HSPH1, METTL7A, HSPA1B, SLC25A37, VIPR1, FAR2, HSPA6, PHC2, PELI1, POLR1E, SPON2, GFOD1, SPRY1, NDFIP1, MAN2A2, ISG20, RAB31, wherein an increase in the gene signature score indicates a response to the glucocorticoid.

In Vivo Assessment of the Glucocorticoid Gene Signature

Figure 3A:
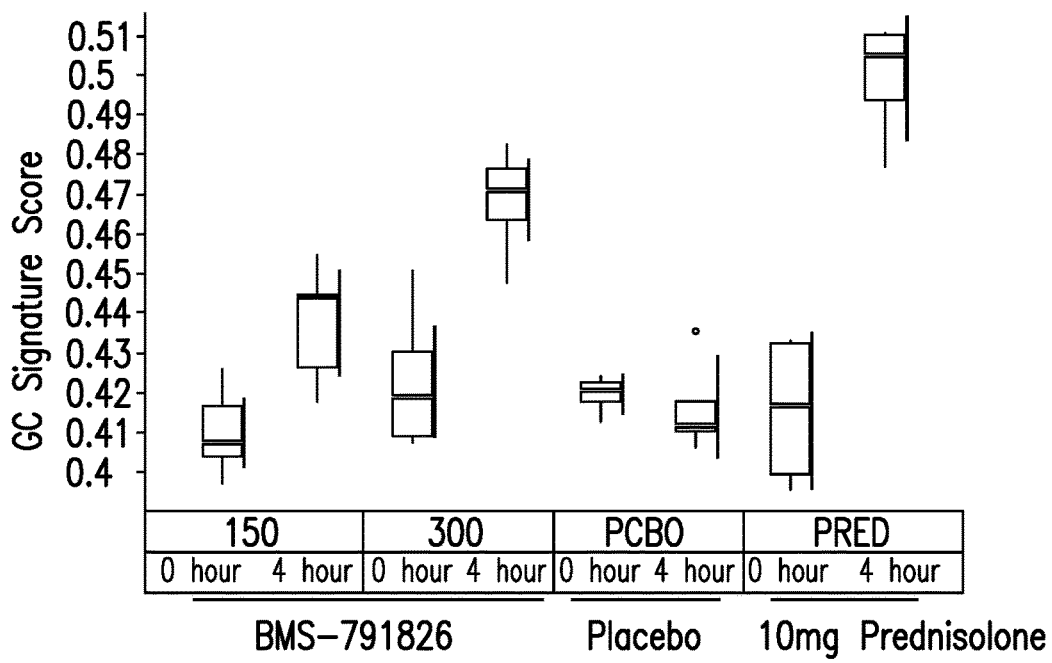
FIG. 3A-3B shows in vivo validation of the GC gene signature. (3A) NHVs were administered an oral dose of 150 or 300 mg GR modulator BMS-791826, 10 mg prednisolone, or placebo. Blood was collected before administration and 4 hours post-dosing. Whole blood expression profiles were analyzed for the GC gene signature. *P=0.027; ***P<0.001. (3B) NHVs were administered 5, 10 or 30 mg prednisolone or placebo (i.e. 0 mg). Blood was drawn before administration and at different times post-dosing (2, 4, 8, 48, 144, and 216 hours). Whole blood expression profiles were analyzed for the GC gene signature.
Figure 3B:
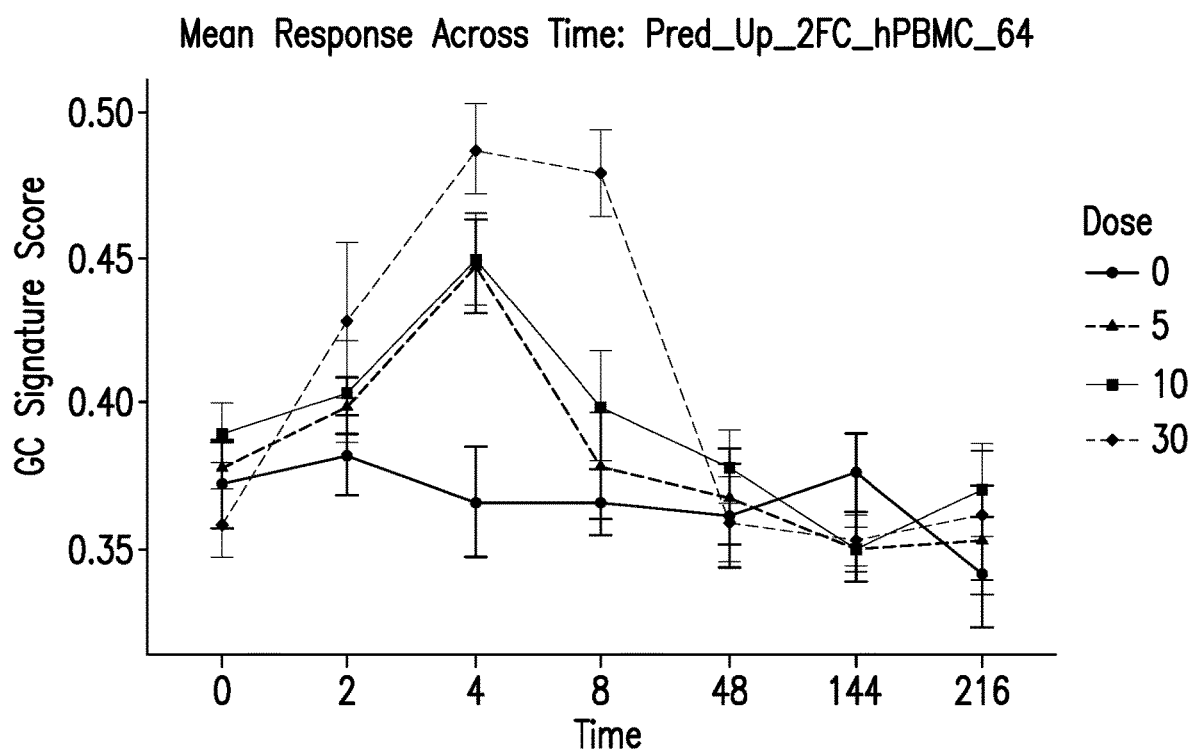

Since the glucocorticoid (GC) signature accurately captured glucocorticoid receptor (GR) agonist activity in vitro, the behavior of the GC gene signature in vivo was tested. Normal healthy volunteers (NHV) were dosed with placebo, 10 mg prednisolone, or 150 or 300 mg GR modulator BMS-791826. Blood was drawn before and 4 hours post-dosing, and RNA was analyzed by Affymetrix gene expression profiling. The GC signature scores for participants dosed with prednisolone were significantly elevated at the 4-hour time point relative to pre-dose and placebo (FIG. 3A). The signature scores for participants dosed with BMS-791826 were higher than predose levels and for those participants given placebo, but lower than those for participants in the prednisolone group. To address the kinetics of the GC gene signature response, whole blood RNA profiles from NHVs who were administered different doses of prednisolone was analyzed. The GC gene signature score increased dose dependently and peaked at 4 hours post-dose (FIG. 3B). For all but the highest dose of prednisolone, GC gene signature scores had returned to baseline levels by 8 hours post-dose. The signature score was at baseline levels in all groups by 48 hours post-dosing.

The composite glucocorticoid gene signature score is a sensitive measure of in vivo responses to glucocorticoid administration.

The invention comprises a method to determine a person's response to prednisolone comprising administering prednisolone to said person, drawing blood from the person administered prednisolone 4 hours post-administration, isolating the RNA from the collected blood, profiling the gene expression of the isolated RNA, and comparing the gene signature score post-administration with a control gene signature score, wherein the gene signature comprises genes ECHDC3, ACSL1, P2RX5, TPST1, TBC1D8, APBA2, SESN1, RNASE1, ABLIM3, RNASE6, BLM, KIF13B, DNMBP, SAP30, SFMBT1, TMEM2, HSPH1, METTL7A, HSPA1B, SLC25A37, VIPR1, FAR2, HSPA6, PHC2, PELI1, POLR1E, SPON2, GFOD1, SPRY1, NDFIP1, MAN2A2, ISG20, RAB31, wherein an increase in the gene signature score indicates a response to prednisolone.

Figure 4A:
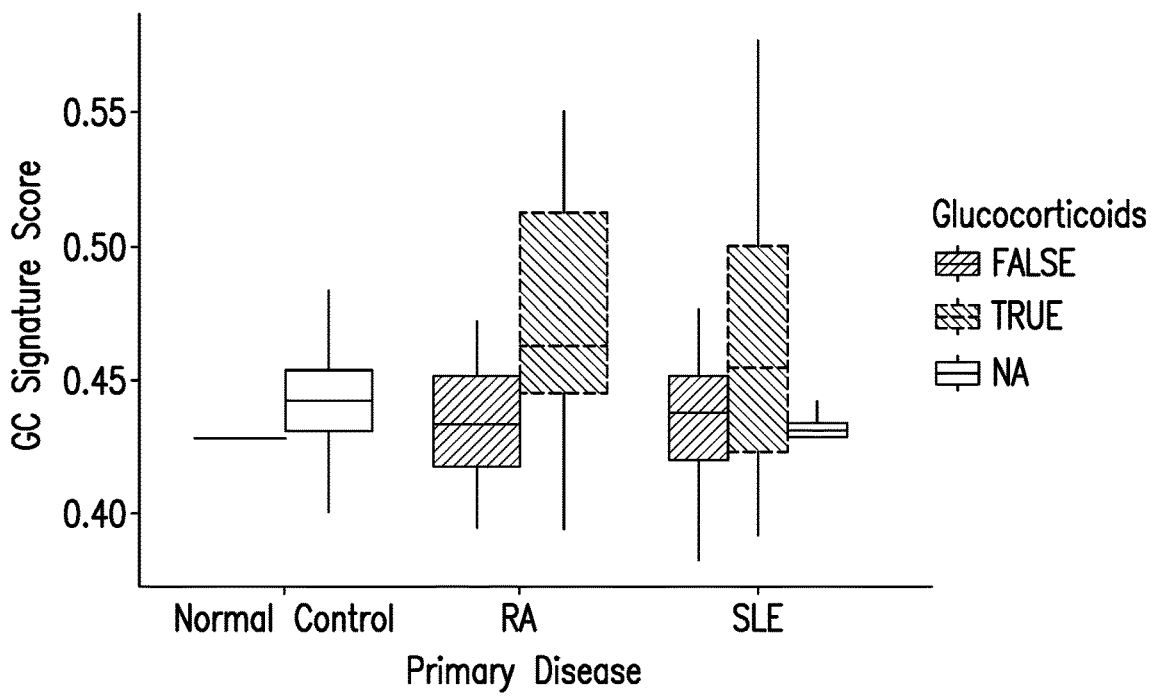
FIG. 4A-4B shows the relationship of the GC gene signature to GC use in SLE and RA cohorts. (4A) Whole blood was collected from NHVs and patients with RA and SLE. RNA was isolated and used to probe Affymetrix HG-219 arrays. GC gene signature scores are divided by patients currently using GCs (true) versus patients on other standard-of-care treatments (false). Patients without treatment information are listed under 'NA' (not available).
Figure 4B:
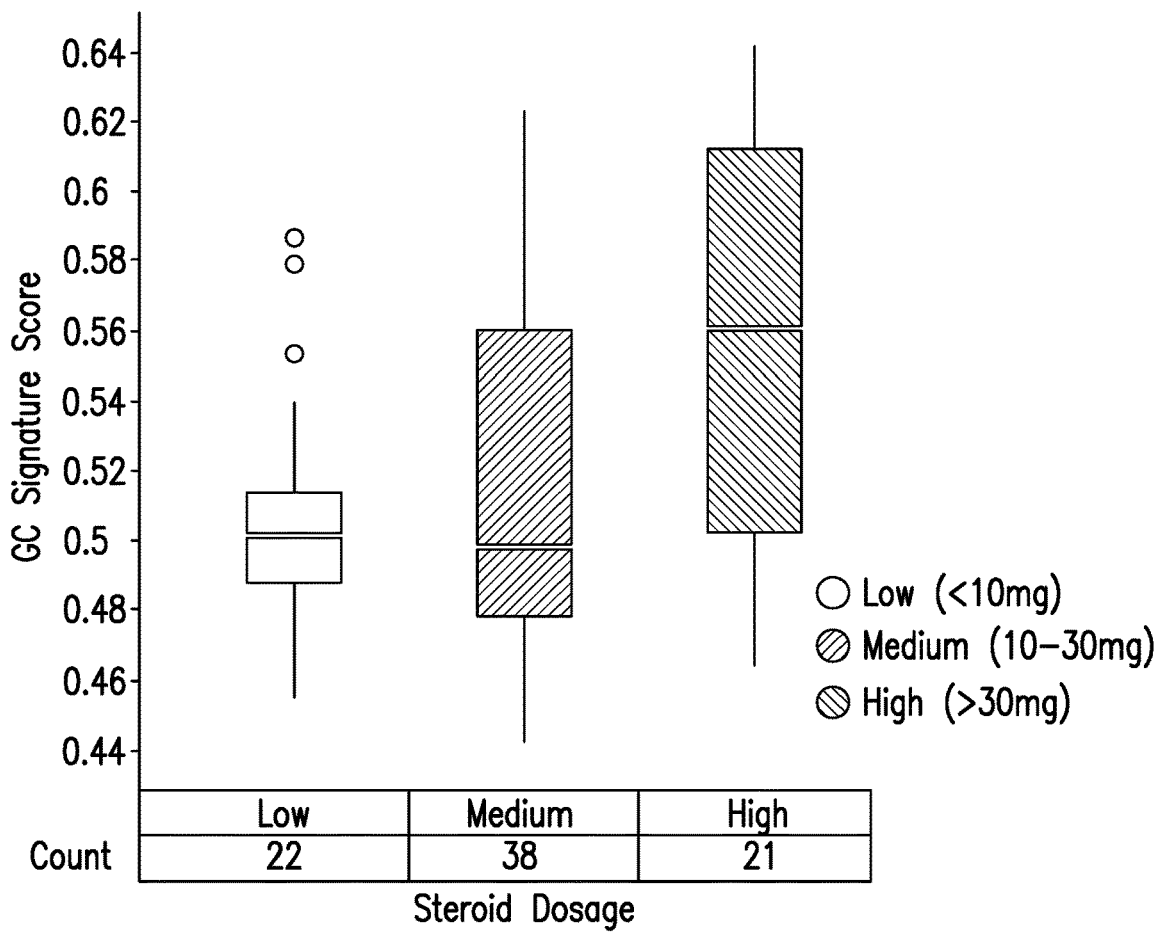

Relationship of the Glucocorticoid Gene Signature with Reported Glucocorticoid Use To determine if the glucocorticoid signature could differentiate between patients based on treatment status, expression of the signature in cross-sectional cohorts of patients with SLE or RA were analyzed. Relative to either normal healthy controls or patients treated with other standard-of-care medications, the patients with SLE or RA who were prescribed glucocorticoids had elevated signature scores (FIG. 4A). While the glucocorticoid signatures were elevated, there was significant inter-patient variability in the signature scores. Baseline samples from a phase II study of abatacept in SLE was analyzed (Fleishaker D L, et. al., BMC Musculoskelet Disord 2016; 17:29) for expression of the glucocorticoid gene signature (FIG. 4B). The glucocorticoid gene signature scores generally aligned well with reported prednisone dose when categorized into high (>30 mg), medium (10-30 mg) and low (<10 mg) doses. However, there was again significant inter-patient variability in glucocorticoid gene signature scores in all groups. This could reflect steroid resistance in some patients or compliance issues with some patients.

Correlation of the Glucocorticoid Gene Signature with Other Pharmacodynamic Endpoints Glucocorticoids are known to cause redistribution of leukocyte subsets through demargination of neutrophils from the bone marrow or sequestration of lymphocyte populations in lymphoid organs (Merayo-Chalico J, et. al., Hum Immunol 2016; 77:921-6; Spies C M, et. al., Arthritis Res Ther 2014; 16 Suppl 2:S3). To determine if the glucocorticoid signature correlated with these pharmacodynamic endpoints, peripheral blood of SLE and RA patients were tested for CD4+ T cells, CD8+ T cells, and CD19+ B cells. Expression of the glucocorticoid signature was negatively correlated with the percentages of these subsets in the peripheral blood of SLE patients (FIG. 5A) and RA patients (FIG. 5B). In the abatacept SLE trial, the glucocorticoid signature scores were positively correlated with neutrophil counts (FIG. 5C).

Therefore, expression of the glucocorticoid gene signature correlates with the known biology of glucocorticoids in both SLE and RA patients.

Refinement of the Glucocorticoid Gene Signature

Further refinement of the 64 member gene signature would facilitate implementation in the clinic. The list of 64 upregulated genes was refined to those upregulated genes that were induced by greater than 1.5-fold with a FDR-adjusted P value of <0.05 comparing patients dosed with prednisolone versus placebo in the Prednisoline in Healthy Male cohort 2 trial. The list was further filtered for detectable expression in the abatacept SLE trial. Of the initial 64 genes, 18 (FKBP5, ECHDC3, IL1R2, ZBTB16, IRS2, IRAK3, ACSL1, DUSP1, PHC2, TLR2, TSC22D3, SLA, CRISPLD2, MAN2A2, FAR2, CEBPD, SPTLC2, HSPA6) met these criteria. The top 3 genes (FKBP5, ECHDC3 and IL1R2), top 6 genes (FKBP5, ECHDC3 IL1R2, ZBTB16, IRS2, IRAK3) and top 8 genes (FKBP5, ECHDC3, IL1R2, ZBTB16, IRS2, IRAK3, ACSL1, DUSP1) from the list were then used to calculate ssGSEA scores.

| GeneSymbol | logFC | adj. P. Val | AveExpresion | OrderIn18 |
|---|---|---|---|---|
| FKBP5 | 2.85 | 6.93E−05 | 5.08 | 1 |
| ECHDC3 | 2.34 | 6.52E−05 | 4.18 | 2 |
| IL1R2 | 2.07 | 7.12E−04 | 7.80 | 3 |
| ZBTB16 | 2.04 | 5.92E−05 | 5.79 | 4 |
| IRS2 | 1.75 | 1.36E−03 | 7.51 | 5 |
| IRAK3 | 1.45 | 9.77E−03 | 4.25 | 6 |
| ACSL1 | 1.43 | 4.41E−03 | 8.46 | 7 |
| DUSP1 | 1.37 | 2.30E−04 | 5.13 | 8 |
| PHC2 | 1.15 | 5.92E−05 | 10.13 | 9 |
| TLR2 | 1.11 | 1.54E−03 | 9.35 | 10 |
| TSC22D3 | 1.08 | 7.76E−03 | 9.23 | 11 |
| SLA | 0.98 | 2.42E−04 | 9.20 | 12 |
| CRISPLD2 | 0.94 | 5.54E−03 | 7.60 | 13 |
| MAN2A2 | 0.91 | 3.73E−04 | 5.43 | 14 |
| FAR2 | 0.88 | 1.37E−02 | 5.39 | 15 |
| CEBPD | 0.86 | 8.78E−05 | 9.50 | 16 |
| SPTLC2 | 0.75 | 1.05E−03 | 5.21 | 17 |
| HSPA6 | 0.67 | 7.76E−03 | 7.21 | 18 |

Analysis of the Prednisoline in Healthy Male cohort 2 study of the partial GR agonist with this abbreviated signature fully captured the behavior of the 64-gene signature (FIG. 6A). Similar to the signature generated with the 64 upregulated genes, the 8-gene signature accurately reflected the transactivation potential of the partial agonist and prednisolone following in vivo administration of these compounds. The 8-gene signature also positively correlated with peripheral blood neutrophil counts from the abatacept SLE trial, with a similar P value as for the correlation generated with the 64-gene list (FIG. 6B). We conclude that a quantitative polymerase chain reaction (qPCR) assay for these 8 genes would be a sensitive biomarker of glucocorticoid pharmacodynamic activity that can be implemented with a simple whole blood collection.

The invention comprises a method to determine a person's response to prednisolone comprising administering prednisolone to said person, drawing blood from the person administered prednisolone 4 hours post-administration, isolating the RNA from the collected blood, profiling the gene expression of the isolated RNA, and comparing the gene signature post-administration with a control gene signature, wherein the gene signature comprises genes FKBP5, ECHDC3, IL1R2, ZBTB16, IRS2, IRAK3, ACSL1, DUSP1, wherein an increase in the gene signature score indicates a response to prednisolone.

The invention comprises a method to determine a person's response to prednisolone comprising administering prednisolone to said person, drawing blood from the person administered prednisolone 4 hours post-administration, isolating the RNA from the collected blood, profiling the gene expression of the isolated RNA, and comparing the gene signature post-administration with a control gene signature, wherein the gene signature comprises genes FKBP5, ECHDC3, IL1R2, ZBTB16, IRS2, IRAK3, ACSL1, DUSP1, PHC2, TLR2, TSC22D3, SLA, CRISPLD2, MAN2A2, FAR2, CEBPD, SPTLC2, HSPA6 wherein an increase in the gene signature score indicates a response to prednisolone.

The invention comprises a method to determine a person's response to prednisolone comprising administering prednisolone to said person, drawing blood from the person administered prednisolone 4 hours post-administration, isolating the RNA from the collected blood, profiling the gene expression of the isolated RNA, and comparing the gene signature post-administration with a control gene signature, wherein the gene signature comprises genes FKBP5, ECHDC3, IL1R2, wherein an increase in the gene signature indicates a response to prednisolone.

The invention comprises a method to determine a person's response to prednisolone comprising administering prednisolone to said person, drawing blood from the person administered prednisolone 4 hours post-administration, isolating the RNA from the collected blood, profiling the gene expression of the isolated RNA, and comparing the gene signature post-administration with a control gene signature, wherein the gene signature comprises genes FKBP5, ECHDC3, IL1R2, ZBTB16, IRS2, IRAK3, wherein an increase in the gene signature score indicates a response to prednisolone.

Conclusion

Glucocorticoids remain a mainstay of treatment for many autoimmune and inflammatory diseases due to their potent anti-inflammatory activity. Chronic use is, however, associated with an increased risk of toxic effects. Given this risk and the significant inter-patient variability in the clinical response to glucocorticoids, there is a need for a sensitive, objective pharmacodynamic that will facilitate proper dose selection.

The glucocorticoid gene signature of the invention was developed based on in vitro expression-profiling experiments using PBMCs derived from NHVs. Genes induced by glucocorticoid treatment, rather than downregulated genes, were focused on due to a larger dynamic range across donors. The ssGSEA algorithm was used to generate a composite score that can be applied to individual samples or patients. This algorithm appeared to sensitively detect glucocorticoid-dependent transcriptional responses based on several observations. The glucocorticoid signature score accurately reflected the transactivation potential of synthetic partial GR agonists from both in vitro whole blood profiling studies and in vivo studies using samples obtained following oral administration of full and partial GR agonists. The signature scores also captured the dose response to glucocorticoid both in vitro and in vivo.

When the method of the invention was applied to samples from cross-sectional cohorts of patients with SLE and RA, glucocorticoid signature scores were higher in patients using glucocorticoids compared with those on other non-glucocorticoid standard-of-care medications. In baseline samples from an abatacept SLE trial, glucocorticoid signature scores progressively increased as steroid doses increased.

The glucocorticoid gene signature of the invention has utility not only as part of clinical practice, but also in helping to determine the potential confounding effects of steroids in clinical trials. In baseline samples from the abatacept SLE trial, glucocorticoid gene signature scores generally correlated with reported steroid dosage. However, significant inter-patient variability within each dose group was observed. The method of the invention can be used to determine if a patient is resistance to glucocorticoids or not adherent to the study protocol.

Given the strong anti-inflammatory effects of glucocorticoids, trials often include a requirement to either taper or even discontinue glucocorticoids. The glucocorticoid gene signature of the invention provides an objective method with which to assess compliance to the protocol. Calculation of the 8-gene signature score can easily be conducted with qPCR or other platforms using whole blood collections. In summary, the gene signature of the invention has broad utility for monitoring responses to glucocorticoids in the many indications for which they are prescribed.

Example 1

Identification of Glucocorticoid-Regulated Genes

Lymphocytes were isolated from the blood of 10 independent donors using Ficoll gradient centrifugation. Cells were cultured at 5 million lymphocytes/well of a 96-well flat-bottom block plate (Qiagen, Hilden, Germany) in 500 µl assay media (RPMI-1640 with GlutaMAX, 10% charcoal-stripped fetal bovine serum; Gibco Laboratories, Gaithersburg, Md., USA). Cells were cultured for 6 hours with either dimethyl sulfoxide (DMSO) vehicle or 1 µM prednisolone. After 6 hours, cells were pelleted and resuspended in 1 ml nucleic acid purification lysis solution (Applied Biosystems, Foster City, Calif., USA) diluted 1:2 with calcium and magnesium-free phosphate-buffered saline (Invitrogen, Carlsbad, Calif., USA). Cells were incubated in lysis buffer for 10 min at room temperature followed by storage at −80° C. RNA was isolated using the Qiagen RNeasy isolation kit according to manufacturer's instructions.

For profiling of whole blood, anticoagulant citrate dextrose solution A-containing whole blood from 4 normal healthy volunteers was cultured with either DMSO vehicle, 200 nM prednisolone, 1 µM prednisolone, 5 µM prednisolone, 5 µM GR modulators BMS-791826, or 10 µM BMS-776532 for 5 hours, followed by transfer to a PAXgene tube. Total RNA was isolated, and then treated with DNase I and cleaned up using a Qiagen RNeasy MinElute Cleanup Kit. RNA concentrations were determined using NanoDrop (Thermo Fisher Scientific, Waltham, Mass., USA) and RNA quality was evaluated using the Experion electrophoresis system (Bio-Rad Laboratories, Hercules, Calif., USA). All target labeling reagents were purchased from Affymetrix (West Sacramento, Calif., USA).

Double-stranded cDNAs were synthesized from 1 µg of total RNA through reverse transcription with an oligo-dT primer containing the T7 RNA polymerase promoter and double-strand conversion using the cDNA Synthesis System (Invitrogen, Carlsbad, Calif., USA). Biotin-labeled cRNA was generated from the cDNA and used to probe a Human Genome HT_HG-U133A plate (Affymetrix, Sunnyvale, Calif., USA), consisting of 96 single HG-U133A arrays in a 96-well plate. All cDNA and cRNA target preparation steps were processed on a Caliper GeneChip Array Station from Affymetrix. Array hybridization, washing, and scanning were performed according to the manufacturer's recommendations.

Gene Signature Development and Scoring

CEL files from the Affymetrix Array Station were processed and normalized using the Robust Multi-Array Average (RMA) algorithm (Gautier I, et. al., Bioinformatics 2004; 20:307-15) using the "Affy" package in R (version 3.2.1; 16) and Bioconductor (Gentleman R C, et. al. Genome Biol. 2004, 5 (10):R80) with custom CDF files from BrainArray (version 18.0.0; Dai M, et. al., Nucleic Acids Res 2005; 33:e175). Differential gene expression analysis was run to compare gene expression levels in prednisolone-treated versus control samples, using a moderated t-test (Ritchie M E, et. al., Nucleic Acids Res 2015; 43:e47) in Array Studio (OmicSoft, Cary, N.C., USA). P values were adjusted using the multiple test correction method which is also called false discovery rate (FDR, Benjamini Y, et. al., J. Royal Statistical Soc., Series B 1995; 57:289). Genes that were upregulated or downregulated by at least 2-fold with an adjusted P value of <0.05 across experiments were reported as the GC gene signatures.

To score an individual sample by the enrichment level of GC gene signatures, we adapted the single-sample gene set enrichment analysis (ssGSEA) algorithm (Barbie D A, et. al., Nature 2009; 462:108-12) to generate a composite score, which was implemented using the Gene Set Variation Analysis package in R (version 3.4.0, Hanzelmann S, et. al., BMC Bioinformatics 2013; 14:7). The algorithm was modified so that enrichment scores fell between −1 and 1, representing the lowest to the highest possible rankings of GC genes in the transcriptome.

Mammalian 2-Hybrid Analysis

Sequences encoding either full-length human peroxisome proliferator-activated receptor γ coactivator-1alpha (PGC1α) or full-length human transcriptional mediators/intermediary factor 2 (TIF2) were cloned in frame with the GAL4 DNA-binding domain in the vector pM (Clontech, Mountain View, Calif., USA). Full-length human GR was cloned in frame with the VP16 activation domain in the vector pVP16 (Clontech). Human SK-N-MC neuroblastoma cells (American Type Culture Collection, Manassas, Va., USA) were co-transfected with these plasmids and a GAL4-dependent luciferase reporter (pGF-luc; Promega, Madison, Wis., USA). Transfectants were stimulated with either 200 nM dexamethasone or different concentrations of prednisolone, GR modulators BMS-791826, or BMS-776532. Luciferase activity was measured 48 hours post transfection.

Chromatin Immunoprecipitation

For chromatin immunoprecipitations, A549 cells were cultured for 1 hour with either DMSO, 1 µM prednisolone, 1 µM GR modulators BMS-791826, or 2 µM BMS-776532 in RPMI with 10% charcoal-stripped fetal calf serum. Cells were fixed with formaldehyde and sent to Active Motif (Carlsbad, Calif., USA) for analysis of GR and TIF2 recruitment to specific promoter sequences using quantitative polymerase chain reaction (qPCR).

Patient Cohorts

Systemic Lupus Erythematosus (SLE) and Rheumatoid Arthritis (RA) Cross-Sectional Cohorts Peripheral blood was obtained in 2014 and 2015 from 86 patients with SLE during routine visits at Northwell Health (Great Neck, N.Y., USA). The patients were on standard-of-care treatment for general SLE or lupus nephritis that included hydroxychloroquine, mycophenolate mofetil, glucocorticoids, and/or belimumab. Patient characteristics were as follows: age, 45±14 years (mean±SD); female, 85%; SLE Disease Activity Index 2000 score (SLEDAI-2K), 3.7±3.2 (mean±SD); history of lupus nephritis, 43%; duration of disease, 15±13 years (mean±SD).

For the RA cohort, blood was obtained in 2014 and 2015 from 84 patients during routine visits at either Brigham and Women's Hospital, Boston, Mass. or Northwell Health, Great Neck, N.Y. The patients were on standard-of-care treatment for RA that included methotrexate, hydroxychloroquine, tofacitinib, abatacept, anti-tumor necrosis factor biologics, tocilizumab, glucocorticoids, and/or non-steroidal anti-inflammatory agents. Patient characteristics were as follows: age, 57±14 years (mean±SD); female, 77%; 2010 American College of Rheumatology criteria for rheumatoid arthritis score, 7.8±1.6 (mean±SD); duration of disease, 17±10 years (mean±SD). A PAXgene tube of blood was collected at each visit, as well as heparinized blood. Blood was shipped overnight and processed on arrival for fluorescence-activated cell-sorting analysis. PAXgene tubes of blood were also collected from age- and sex-matched normal healthy volunteers (Bristol-Myers Squibb, Princeton, N.J., USA). RNA was isolated from PAXgene tubes of blood and used to probe Affymetrix HG-U219 gene arrays using the protocols described above.

Abatacept SLE Clinical Cohort (NCT00119678)

Baseline PAXgene collections and complete blood counts were obtained from 144 adults with SLE meeting the criteria of a British Isles Lupus Assessment Group (BILAG) score of A or B. The population at baseline consisted of 53% of patients with polyarthritis, 35% with discoid lupus, and 12% with serositis. Overall, 87% of patients were on prednisone, 50% were on hydroxychloroquine, and 41% were on immunosuppressives (methotrexate, azathioprine, or mycophenolate mofetil).

Prednisoline in Healthy Male Cohort 1 (NCT03196557)

Male normal healthy volunteers were randomly assigned (6 participants/group) to receive daily doses of 5, 10, or 30 mg prednisolone for 7 days. Two participants received placebo. PAXgene tubes were collected before dosing and at 2, 4, 8, 48, 144, and 216 hours post-dose.

Prednisoline in Healthy Male Cohort 2 (NCT03198013)

Male normal healthy volunteers were randomly assigned to receive either a placebo of polyethylene glycol (PEG)-400 solution (4 participants); a single daily oral dose of GR modulator BMS-791826 (150 or 300 mg) as a PEG-400 solution (6 participants/dose); or a single daily dose of 10 mg prednisolone (4 participants) for 3 consecutive days. PAXgene tubes were collected before dosing and at 4 hours post-dose on day 1.

Peripheral Blood Phenotyping

Heparinized whole blood was stained with premixed cocktails of antibodies followed by lysis and fixation. Antibodies used for the SLE panel included CD3-eF450 (clone OKT3; eBioscience, San Diego, Calif., USA), CD4-PE-Cy7 (clone OKT4; BioLegend, San Diego, Calif., USA), CD8-APC-H7 (clone SK1; BD Biosciences, San Jose, Calif., USA), and CD19-BV421 (clone HIB19; BioLegend).

Antibodies used for the RA panel included CD19-BV421, CD3-Ax700 (clone OKT3; BioLegend), CD4-Percp-Cy5.5 (clone RPA-T4; eBioscience), and CD8-Bv785 (clone RPA-T8; BioLegend).

What is claimed is:

1. A method of treating a person diagnosed with rheumatoid arthritis (RA) comprising testing the person's response to a glucocorticoid comprising:
   a. administering the glucocorticoid of interest to said person;
   b. drawing blood from the person of step (a) post-administration;
   c. isolating RNA from the blood collected in step (b);
   d. profiling gene expression of the RNA isolated in step (c);
   e. calculating and comparing gene signature score post-administration with a control gene signature score;
   f. detecting an increase in the gene signature score for FKBP5, ECHDC3, IL1R2, ZBTB16, IRS2, IRAK3, ACSL1, and DUSP1 as indicative indicates that the person will respond to the glucocorticoid; and
   g. administering the glucocorticoid to the person having the increase in the gene signature score in step (f).

2. A method of treating a person diagnosed with systemic lupus erythematosus (SLE) comprising testing the person's response to a glucocorticoid comprising:
   a. administering the glucocorticoid of interest to said person;
   b. drawing blood from the person of step (a) post-administration;
   c. isolating RNA from the blood collected in step (b);
   d. profiling gene expression of the RNA isolated in step (c);
   e. calculating and comparing gene signature score post-administration with a control gene signature score;
   f. detecting an increase in the gene signature score for FKBP5, ECHDC3, IL1R2, ZBTB16, IRS2, IRAK3, ACSL1, and DUSP1 as indicative that the person will respond to the glucocorticoid; and
   g. administering the glucocorticoid to the person having the increase in the gene signature score in step (f).

3. The method of claim 1, wherein the blood sample is collected from the person administered the glucocorticoid of interest 4 hours post-administration.

4. The method of claim 2, wherein the blood sample is collected from the person administered the glucocorticoid of interest 4 hours post-administration.

5. The method of claim 1, wherein the glucocorticoid of interest is selected from the group consisting of cortisone, dexamethasone, hydrocortisone, methylprednisolone, prednisolone, prednisone, triamcinolone, betamethasone budesonide, fluticasone, and synthetic glucocorticoids.

6. The method of claim 1, wherein the control gene signature is obtained from the same person before glucocorticoid administration or from normal healthy controls not administered the glucocorticoid.

7. The method of claim 1, wherein a 1.5-fold increase in the gene signature score compared to the control indicates a response to the glucocorticoid.

8. The method of claim 1, wherein a 2-fold increase in the gene signature score compared to the control indicates a response to the glucocorticoid.

9. The method of claim 2, wherein the glucocorticoid of interest is selected from the group consisting of cortisone, dexamethasone, hydrocortisone, methylprednisolone, prednisolone, prednisone, triamcinolone, betamethasone budesonide, fluticasone, and synthetic glucocorticoids.

10. The method of claim 2, wherein the control gene signature is obtained from the same person before glucocorticoid administration or from normal healthy controls not administered the glucocorticoid.

11. The method of claim 2, wherein a 1.5-fold increase in the gene signature score compared to the control indicates a response to the glucocorticoid.

12. The method of claim 2, wherein a 2-fold increase in the gene signature score compared to the control indicates a response to the glucocorticoid.

* * * * *